(12) United States Patent
Yamakawa et al.

(10) Patent No.: US 9,092,008 B2
(45) Date of Patent: Jul. 28, 2015

(54) AUTOMATIC DOCUMENT FEEDER HAVING ION GENERATING FUNCTION, AND IMAGE FORMING APPARATUS PROVIDED WITH THE SAME

(75) Inventors: Kazuhiko Yamakawa, Osaka (JP); Masao Matsui, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 722 days.

(21) Appl. No.: 12/939,283

(22) Filed: Nov. 4, 2010

(65) Prior Publication Data
US 2011/0129271 A1 Jun. 2, 2011

(30) Foreign Application Priority Data
Dec. 2, 2009 (JP) ................................. 2009-274304

(51) Int. Cl.
G03G 15/00 (2006.01)
G03G 21/20 (2006.01)
B65H 1/04 (2006.01)
H04N 1/00 (2006.01)
A61L 9/22 (2006.01)

(52) U.S. Cl.
CPC ............... *G03G 21/206* (2013.01); *B65H 1/04* (2013.01); *A61L 9/22* (2013.01); *B65H 2301/5305* (2013.01); *B65H 2402/44* (2013.01); *B65H 2405/332* (2013.01); *B65H 2405/3321* (2013.01); *B65H 2406/10* (2013.01); *B65H 2406/364* (2013.01); *B65H 2601/212* (2013.01); *H04N 1/00981* (2013.01)

(58) Field of Classification Search
CPC .................. B65H 2301/5305; H04N 1/00978; H04N 1/00981; H04N 1/00984; H04N 1/00986; H04N 1/00989
USPC .......................... 399/92, 93, 98, 99, 100, 367
See application file for complete search history.

(56) References Cited

U.S. PATENT DOCUMENTS

| | | | | |
|---|---|---|---|---|
| 6,972,398 B2 * | 12/2005 | Kang | ............................ | 219/757 |
| 7,953,341 B2 * | 5/2011 | Tobinaga et al. | ............... | 399/92 |
| 7,973,291 B2 * | 7/2011 | Kagawa et al. | ........... | 250/423 R |
| 2003/0072675 A1 * | 4/2003 | Takeda et al. | ................... | 422/22 |
| 2008/0217556 A1 * | 9/2008 | Kagawa et al. | ........... | 250/423 R |
| 2008/0308995 A1 | 12/2008 | Tobinaga et al. | | |
| 2009/0010672 A1 * | 1/2009 | Watanabe | ....................... | 399/92 |

FOREIGN PATENT DOCUMENTS

| | | |
|---|---|---|
| JP | UM-A-4-33045 | 3/1992 |
| JP | 2004-233618 A | 8/2004 |
| JP | 2005-004144 A | 1/2005 |
| JP | 2008-251514 A | 10/2008 |
| JP | 2008-310028 | 12/2008 |
| JP | 2009210892 A * | 9/2009 |

* cited by examiner

*Primary Examiner* — Daniel J Colilla
*Assistant Examiner* — Justin Olamit
(74) *Attorney, Agent, or Firm* — Renner, Otto, Boisselle & Sklar, LLP

(57) ABSTRACT

The automatic document feeder includes a document tray, a document delivery tray, a document feed path, a feed roller, a housing member, and an ion generating unit. The housing member has at least an air intake portion and an air exhaust portion and is designed to accommodate a driving section therein. The ion generating unit is disposed laterally of the driving section within the housing member.

19 Claims, 7 Drawing Sheets

AUTOMATIC DOCUMENT FEEDER HAVING ION GENERATING FUNCTION, AND IMAGE FORMING APPARATUS PROVIDED WITH THE SAME

CROSS REFERENCE

This Nonprovisional application claims priority under 35 U.S.C. §119(a) on Patent Application No. 2009-274304 filed in Japan on Dec. 2, 2009, the entire contents of which are hereby incorporated by reference.

BACKGROUND OF THE INVENTION

The present invention relates to an automatic document feeder having an ion generating function, and an image forming apparatus provided with the same.

It is no exaggeration to say that image forming apparatuses, such as a copier and a printer, are indispensable for offices and the like. Actually, offices are mostly installed with image forming apparatuses. Further, such image forming apparatuses have recently become familiar to us because they are spreading even to standard homes, hospitals and the like.

Among known image forming apparatuses, there are apparatuses of the type configured to supply the image forming section and fixing section thereof with air taken into the housing from around the image forming apparatus and then exhaust the air out of the image forming apparatus. One such image forming apparatus is provided with an air cleaning section configured to prevent harmful substances produced within the apparatus from being discharged out of the apparatus by eliminating harmful substances contained in a flow of air to be exhausted out of the apparatus to clean the air and then supplying negative ions to the air (see Japanese Patent Laid-Open publication No. 2005-4144 for example).

According to the technique described in Japanese Patent Laid-Open publication No. 2005-4144 noted above, it is necessary to eliminate toner particles, dust, ozone and the like produced by the image forming operation of the image forming section and, hence, an ion generating section having electrodes has to be unavoidably disposed at a location adjacent the image forming section and inside the air flow generated around the image forming section. As a result, a problem sometimes occurs that the ion generating efficiency of the ion generating section lowers earlier than expected due to the effect of silicon and the like produced around the image forming apparatus. Therefore, the above-described technique has a problem that the ability to clean air around the image forming apparatus lowers as the duration of use of the image forming apparatus becomes longer.

In cases where a unit having the air cleaning function is positioned outside the image forming apparatus in order to provide a larger distance between the ion generating section and the image forming section, an additional space is necessary for installation of such a unit, which results in a problem that an enlarged space is needed for installation of the image forming apparatus.

A feature of the present invention is to provide an automatic document feeder and an image forming apparatus which are capable of performing the function of generating ions stably over a long time period without upsizing of the device and the apparatus.

SUMMARY OF THE INVENTION

An automatic document feeder according to the present invention has an ion generating function. The automatic document feeder includes a document tray, a document delivery tray, a document feed path, feeding means, a driving section, a housing member, and an ion generating unit.

The document tray is designed to place thereon a document to be subjected to reading. The document delivery tray is designed to receive the document having been subjected to reading. The document feed path is designed to guide the document from the document tray up to the document delivery tray via a document reading position.

The feeding means is configured to apply feeding force onto the document on the document feed path. An example of such feeding means comprises a pickup roller for picking up the document from the document tray, and a single feed roller or plural feed rollers disposed along the document feed path. The driving section is configured to transmit driving power to the feeding means. An example of such a driving section comprises a motor serving as a power source of the feeding force, a gear train or belt or the like connected to the motor, and a circuit board or the like for controlling the motor.

The housing member is disposed rearwardly of the document tray and the document delivery tray. The housing member has at least an air intake portion and an air exhaust portion and is designed to accommodate the driving section therein.

The ion generating unit is disposed laterally of the driving section within the housing member. Usually, the housing member extends over the entire or major part of width of the automatic document feeder on a rear side (deeper side) of the automatic document feeder, whereas the driving section is placed to occupy only a rear part of the document feed path in the widthwise direction of the automatic document feeder. For this reason, a space can be easily provided laterally of the driving section within the housing member for the placement of the ion generating unit.

Thus, it is possible to easily secure a relatively large space for the placement of the ion generating unit having an air cleaning function for example without an increase in the size of the automatic document feeder which would occur due to the provision of the ion generating unit.

Usually, the automatic document feeder is disposed at the uppermost position of an image forming apparatus such as a copier. For this reason, the ion generating unit is not likely to be affected by silicon and the like produced around the image forming section of the image forming apparatus, while ions generated by the ion generating unit can be easily diffused upwardly and scattered all around the apparatus.

Preferably, the automatic document feeder further comprises a fan configured to generate a flow of air passing from the air intake portion toward the air exhaust portion within the housing member, wherein the driving section and the ion generating unit are located on a flow path of the air passing from the air intake portion toward the air exhaust portion. This feature is preferable because the provision of the single fan enables the driving section to be cooled and the ions to be conveyed.

The present invention makes it possible to impart the automatic document feeder and the image forming apparatus with the function of generating ions stably over a long time period while preventing the feeder and the apparatus from being upsized.

The foregoing and other features and attendant advantages of the present invention will become more apparent from the reading of the following detailed description of the invention in conjunction with the accompanying drawings.

DETAILED DESCRIPTION OF THE INVENTION

Figure 1A:
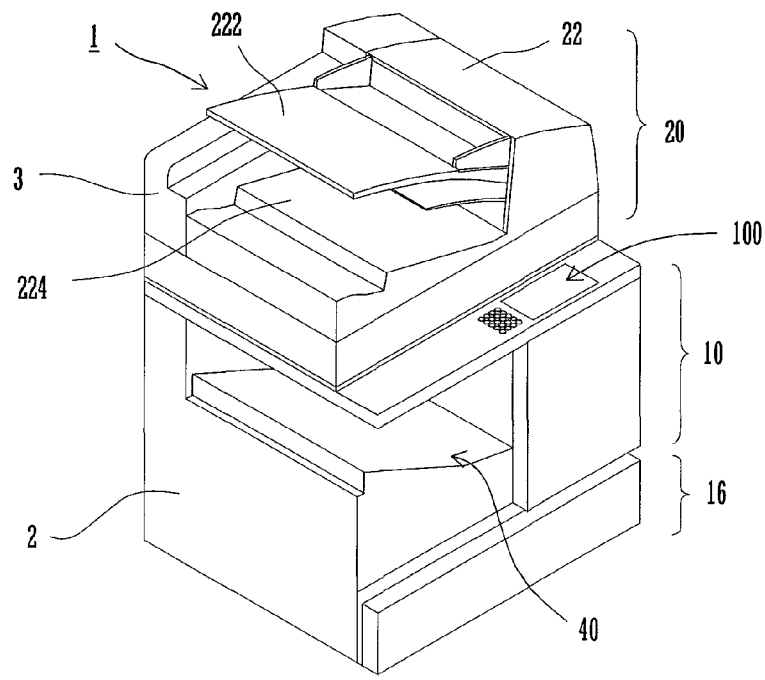
FIG. 1A is a perspective view, as viewed from the front side, of a copier according to an embodiment of the present invention.
Figure 1B:
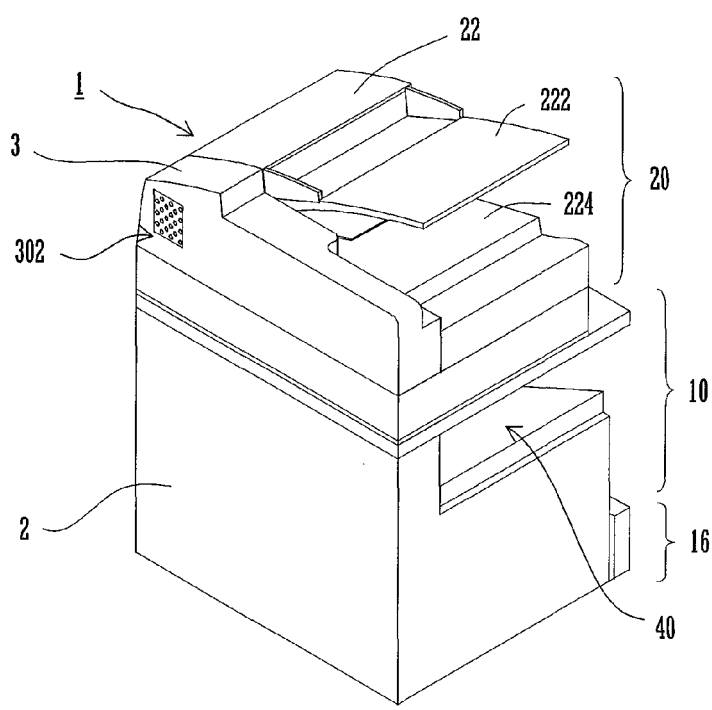
FIG. 1B is a perspective view, as viewed from the rear side, of the copier according to the embodiment of the present invention.
Figure 2:
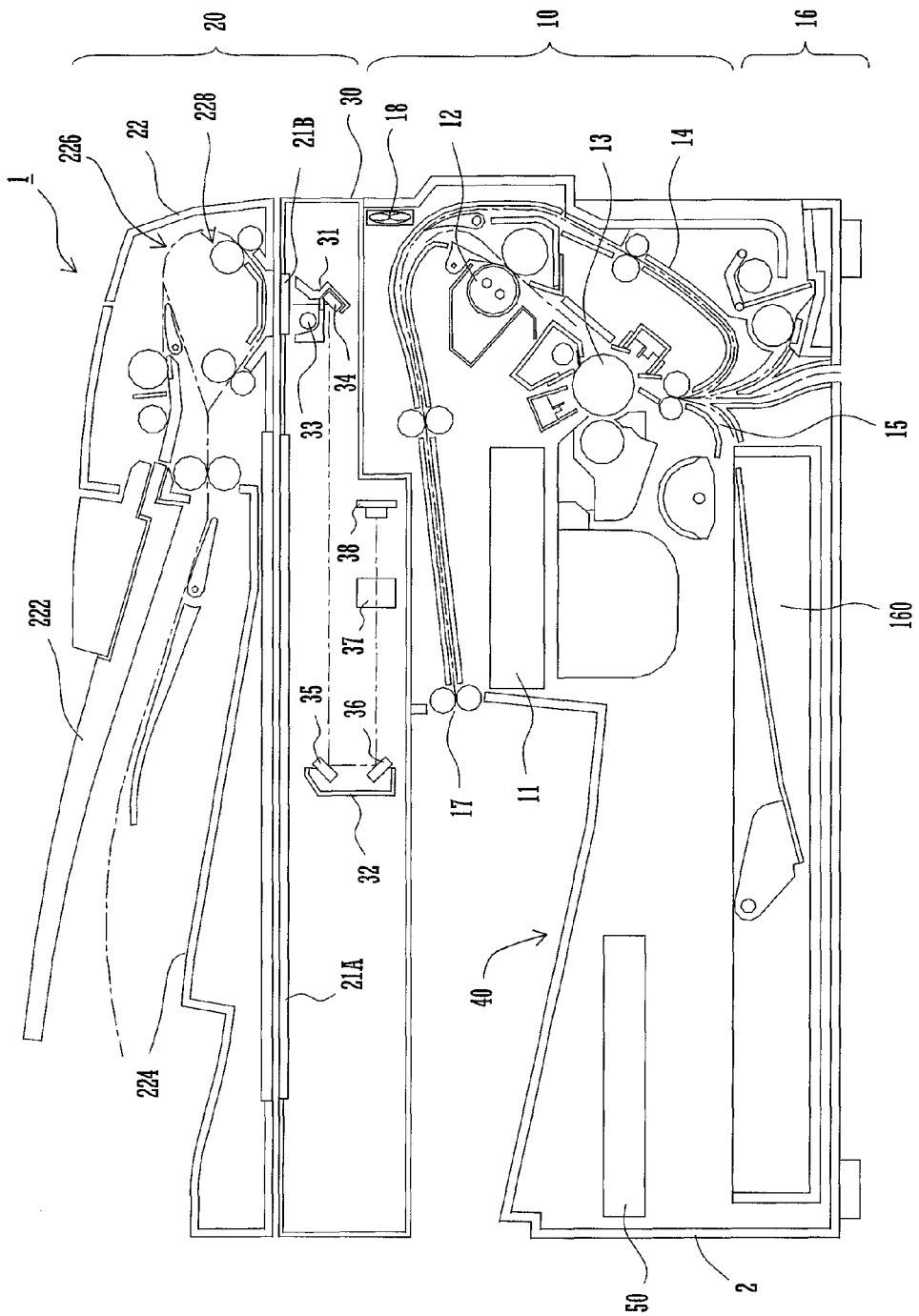
FIG. 2 is a sectional view schematically illustrating the copier according to the embodiment of the present invention.

Referring to FIGS. 1A, 1B and 2, description will be made of the construction of a copier 1 according to an embodiment of the present invention. As shown in these figures, the copier 1 includes a document reading section 20, an image forming section 10, and a sheet feeding section 16. As shown in FIG. 1A, the copier 1 further includes an operating panel 100 on the front side thereof for receiving input operations from the user.

As shown in FIG. 2, the document reading section 20 includes document platens 21A and 21B each formed of transparent glass, a scanner unit 30 configured to read an image from a document placed on the document platen 21A or 21B, and an automatic document feeder 22 for automatically feeding document sheets onto the document platen 21B. The document platen 21A is used for document reading in a document fixing mode, while the document platen 21B used for document reading in a document feeding mode using the automatic document feeder 22.

The automatic document feeder 22 includes a document tray 222 for placing thereon a document to be read, a document delivery tray 224 for receiving a document having been read, and a document feed path 226 formed to guide a document from the document tray 222 up to the document delivery tray 224 via a document reading position (the position of the document platen 21B according to the present embodiment). The document feed path 226 is provided with a plurality of feed rollers 228 arranged to apply a feeding force onto the document in the document feed path 226.

The automatic document feeder 22 automatically feeds plural document sheets set on the document tray 222 onto the document platen 21B one by one through the document feed path 226. The document sheets having been finished with reading at the document platen 21B are delivered onto the document delivery tray 224.

For the scanner unit 30 to read images on both sides of a document according to selection by the user, the automatic document feeder 22 is provided with a feed path for double-sided documents, feed path switching means, a group of sensors for detecting and controlling the states of document sheets passing through different sections, and the like. These components are not essential requirements for carrying out the present invention, but are optional elements.

The scanner unit 30 includes a first scanning unit 31, a second scanning unit 32, an optical lens 37, and a photoelectric converter (hereinafter will be referred to as "CCD") 38. The first scanning unit 31 has a lamp reflector assembly 33 for exposing a document surface to light and a first reflecting mirror 34 for guiding a light image reflected from a document to the CCD 38. The second scanning unit 32 has second and third reflecting mirrors 35 and 36 for guiding the light image from the first scanning unit 31 to the CCD 38. The optical lens 37 directs the light image reflected from the document toward the CCD 38 to form an image on the CCD 38. The CCD 38 converts the light image reflected from the document to an electrical image signal.

The above-described arrangement of the document reading section 20 enables the image on the document placed on the document platen 21A to be read by forming the image on the CCD 38 on a line-by-line basis. The image data read by the scanner unit 30 is transmitted to a non-illustrated image processing section where the image data is subjected to various image processing operations, temporarily stored in a storage section of the copier 1, and then transferred to the image forming section 10 in response to an output instruction.

Within the image forming section 10 a sheet feed path is formed to extend from the sheet feeding section 16 storing therein recording sheets to be subjected to an image forming process to a sheet delivery roller 17 configured to deliver recording sheets to a sheet delivery section 40 of an in-body delivery type (configured to deliver recording sheets to a place inside the body of the copier 1), via the image forming position. The image forming section 10 is provided with a sheet feeding system, a laser writing unit 11, and an electrophotographic processing section 13 for image formation which are arranged along the sheet feed path.

The laser writing unit 11 includes a semiconductor laser light source configured to emit laser light according to image data transferred from the aforementioned document reading section 20 or transmitted from external equipment such as a personal computer, a polygonal mirror configured to deflect the laser light at equal angular velocity, an f-θ lens for correcting the laser light thus deflected at equal angular velocity so that a photosensitive drum in the electrophotographic section 13 is scanned with the laser light at equal velocity.

The electrophotographic processing section 13 includes, around the photosensitive drum as an image carrier, an electrostatic charger for electrostatically charging the photosensitive drum uniformly, a developing device for supplying is developer onto an electrostatic latent image formed on the photosensitive drum by the laser writing unit 11, a transfer device for transferring the resulting developer image from the photosensitive drum to a recording sheet, a separation device for separating the recording sheet from the photosensitive drum, a cleaning device for removing residual developer from the photosensitive drum, and a static eliminator for eliminating static charges from the surface of the photosensitive drum.

At a location on the sheet feed path upstream of the electrophotographic processing section 13, there is disposed a feeding section 15 for feeding a recording sheet stored in a sheet feeding cassette 160 of the sheet feeding section 16 to a transfer position between the photosensitive drum and the transfer device in the electrophotographic processing section 13. At a location on the sheet feed path downstream of the electrophotographic processing section 13, there is disposed a fixing device 12 for fixing the developer image in a state of being attached to but unfixed to the recording sheet onto the recording sheet by heat and pressure. Further, a re-feed path is disposed downstream of the fixing device 12 for re-feeding a recording sheet having been subjected to fixing on the obverse side thereof in order to form an image on the reverse side thereof. An exhaust fan 18 is disposed adjacent the fixing device 12 for exhausting gas produced around the electrophotographic processing section 13 and fixing device 12 out of the copier 1.

The copier 1 has a power source unit 50 disposed above the sheet feeding section 16 and below the sheet delivery section 40. The power source unit 50 is configured to supply electric power to different sections of the copier 1.

Figure 3:
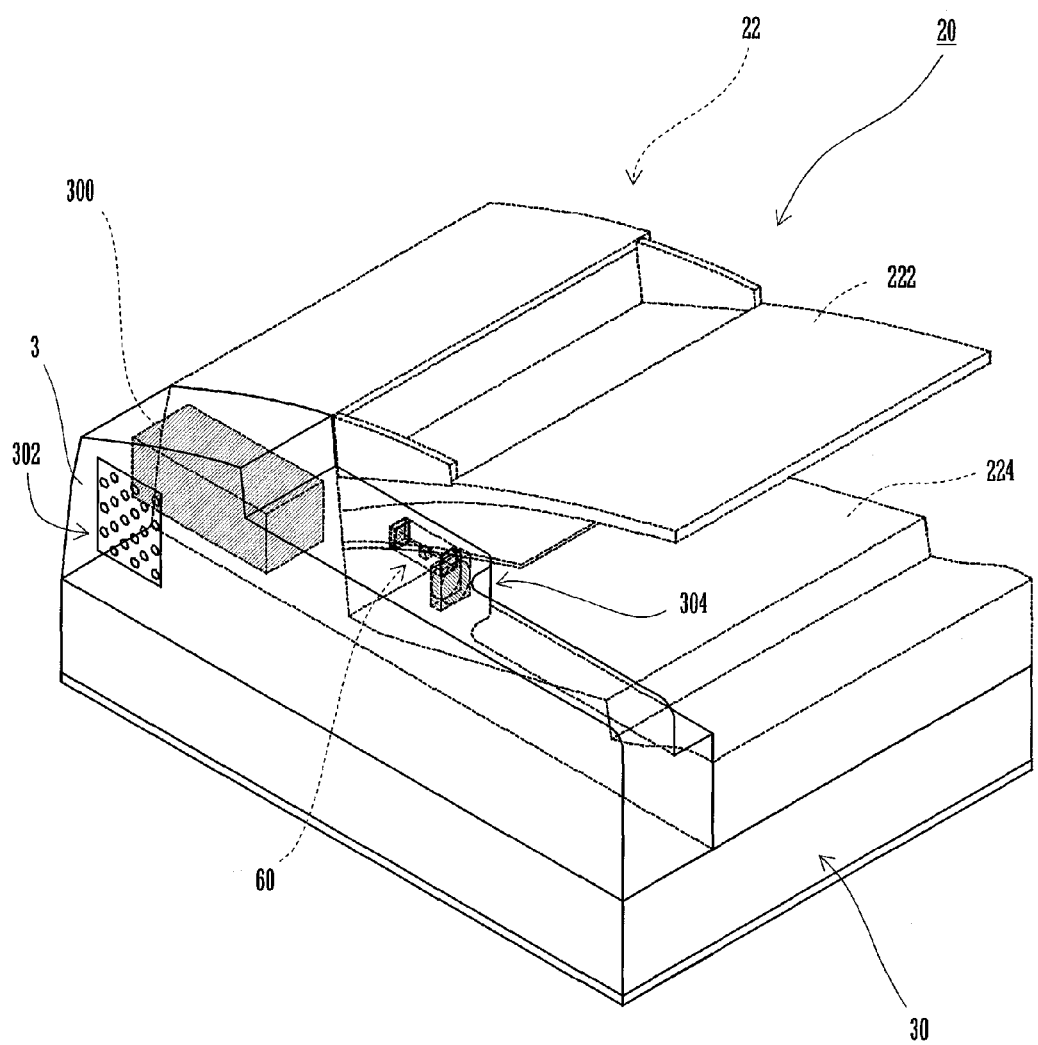
FIG. 3 is a schematic perspective view, as viewed from the rear side, of an image reading section.

Referring to FIG. 3, description is made of an arrangement for imparting the automatic document feeder 22 with an ion generating function. The automatic document feeder 22 includes a driving section 300 configured to transmit driving power to the aforementioned feed roller means 228 and the like. The automatic document feeder 22 further includes a housing member 3.

The housing member 3 is disposed rearwardly of the document tray 222 and the document delivery tray 224. The housing member 3 has an air intake portion 302 for taking outside air therein and an air exhaust portion 304 for exhausting the air taken in (see FIG. 5A) and is designed to accommodate the driving section 300 therein.

Within the housing member 3 an ion generating unit 60 having an ion generating function is disposed laterally of the driving section 300. The ion generating unit 60 is configured to generate positive ions and negative ions in substantially equal amounts by ionizing water vapor contained in the air by corona discharge. In the present embodiment, each positive ion has plural water molecules attracted around a hydrogen ion (H+) and is represented by $H+ (H_2O)_m$ where m is a natural number. On the other hand, each negative ion has plural water molecules attracted around an Oxygen ion ($O_2-$) and is represented by $O_2-(H_2O)_n$ where n is a natural number. When attached onto the surfaces of bacteria floating around the copier 1, such positive ions or negative ions cause chemical reaction to produce hydrogen peroxide ($H_2O_2$) or hydroxyl radical (OH) as active species. Because hydrogen peroxide ($H_2O_2$) and hydroxyl radical (OH) exhibit very strong activity, they can kill bacteria floating in the air.

Figure 4:
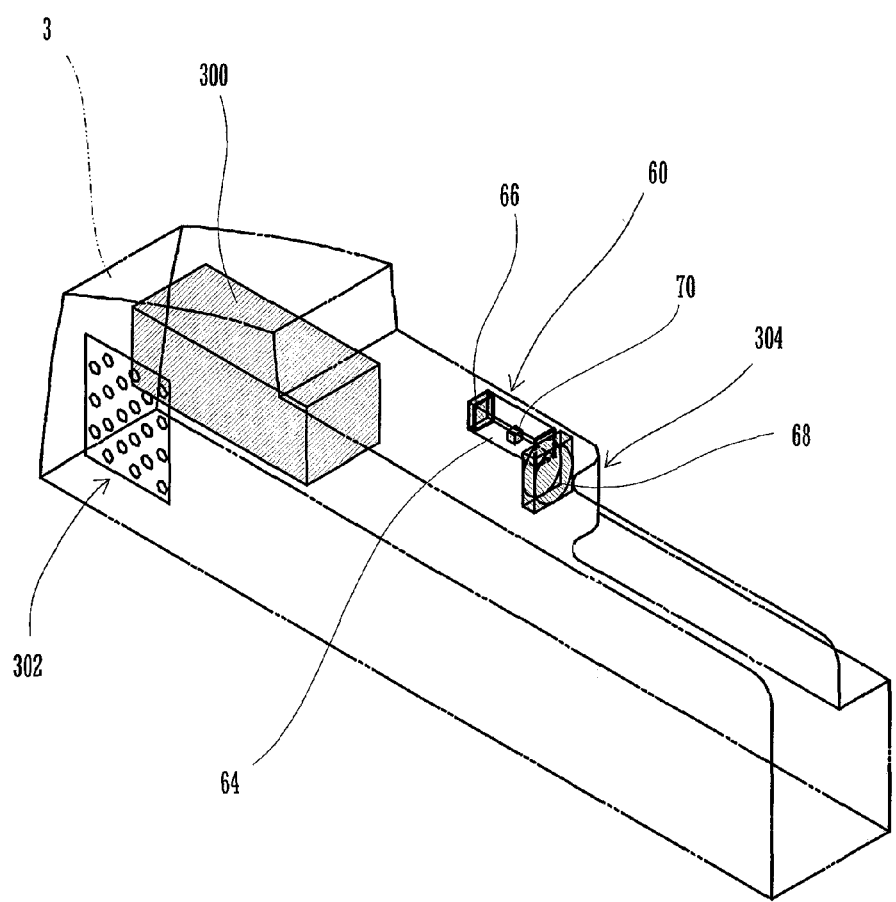
FIG. 4 is a schematic perspective view, as viewed from the rear side, of the housing member accommodating the driving section therein.

Referring to FIG. 4, the structure inside the housing member 3 is schematically described. As shown, the ion generating unit 60 is disposed between the air intake portion 302 and the air exhaust portion 304 within the housing member 3 so as to be located side by side with the driving section 300.

The ion generating unit 60 includes a duct 64, a filter 66, and an ion generating device 70. The duct 64 is designed to define a flow path for guiding air taken therein from the air intake portion 302 to the ion generating device 70. The duct 64 is fixed to an internal frame of the housing member 3 by means of a screw or the like, but the present invention is not limited to this feature.

The filter 66 is located adjacent an end of the duct 64 on the air intake side. The filter 66 is designed to capture dust, oil and the like which are about to enter the duct 64 from the driving section 300. Though it is sufficient in principle that the filter 66 has an ordinary function for capturing dust, use of a filter having a silicon adsorbing function is preferable.

The fan 68 is disposed between the ion generating unit 60 and the air exhaust portion 304. The fan 68 is located adjacent the air exhaust portion 304 within the housing member 3 and is configured to generate a flow of air passing from the air intake portion 302 toward the air exhaust portion 304 within the housing member 3. The air flow generated by the fan 68 cools the driving section 300 while exhausting ions generated by the ion generating device 70 to outside the housing member 3.

The ion generating device 70 is configured to generate positive ions and negative ions in substantially equal amounts by ionizing water vapor contained in the air present in the duct 64 by corona discharge. The structure of the ion generating device 70 is not limited to that according to the present embodiment.

Figure 5A:
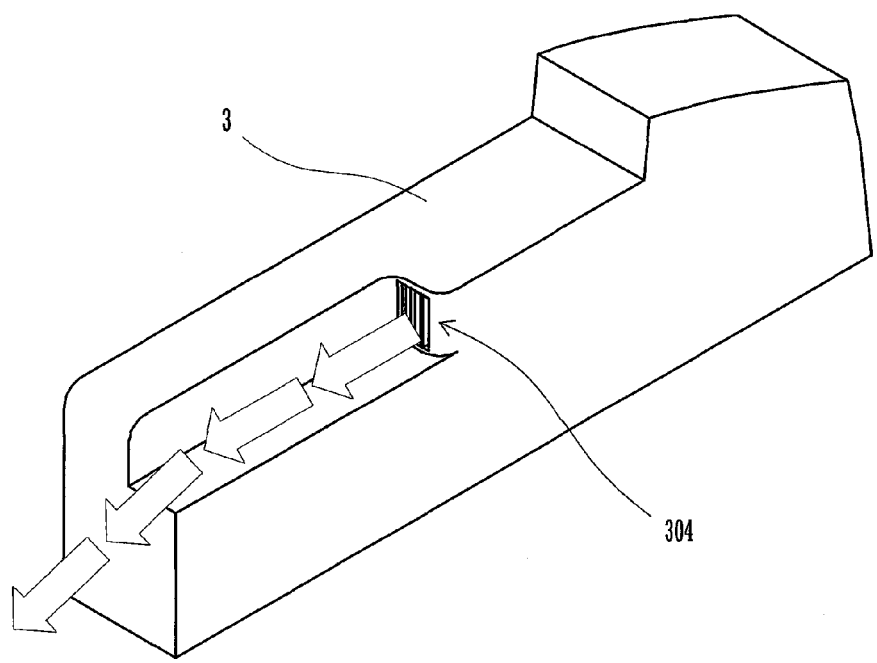
FIG. 5A is a schematic perspective view, as viewed from the front side, of the housing member accommodating the driving section therein.
Figure 5B:
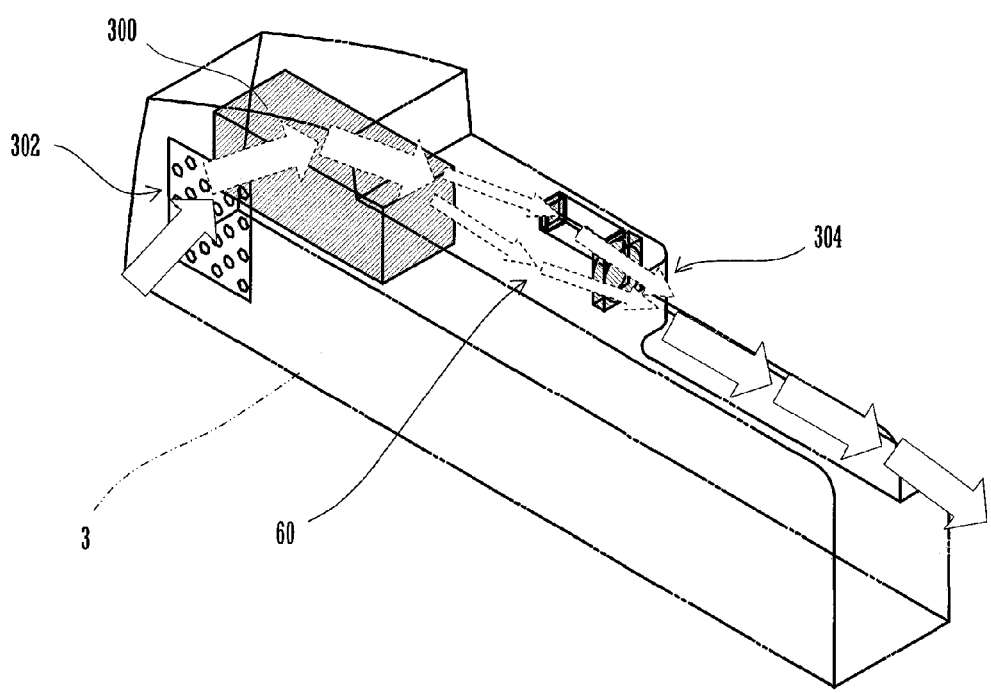
FIG. 5B is a schematic perspective view, as viewed from the rear side, of the housing member accommodating the driving section therein.

Referring to FIGS. 5A and 5B, description is made of an air flow within the housing member 3. As shown in FIG. 5B, air is taken into the housing member 3 from the air intake portion 302 by the suction power of the fan 68. The air thus taken in through the air intake portion 302 flows toward the air exhaust portion 304 through the driving section 300.

Part of the air passing from the driving section 300 toward the air exhaust portion 304 is introduced into the duct 64 and then exhausted in a state of containing ions generated by the ion generating device 70 from the air exhaust portion 304 to the outside.

With this arrangement, even when driving section 300 produces dust and oil, such dust and oil are captured by the filter 66 at the entrance of the duct 64 and hence fail to reach the ion generating device 70. Therefore, the ion generating efficiency of the ion generating device 70 is not lowered by the dust and oil produced by the driving section 300.

The ion generating unit 60 is placed so as to avoid obstructing the flow path of air passing from the driving section 300 directly to the fan 68 as far as possible, thereby securing the flow path of the air passing from the driving section 300 directly to the fan 68. For this reason, the heat dissipation efficiency of a heat generating member, such as a control circuit board, in the driving section 300 is not likely to lower. Further, since the single fan 68 is used to serve the both purposes of cooling the driving section 300 and conveying ions, there is no need to provide an additional fan despite the provision of the ion generating unit 60.

Figure 6A:
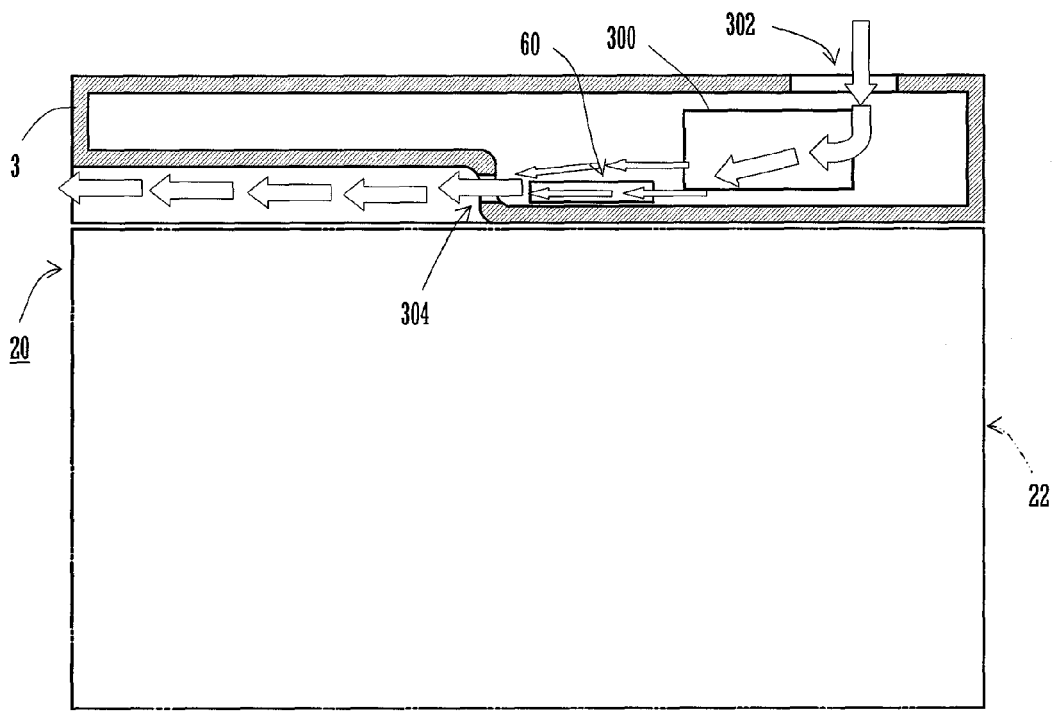
FIG. 6A is a vertical sectional view of the copier for illustrating an air flow inside the copier.
Figure 6B:
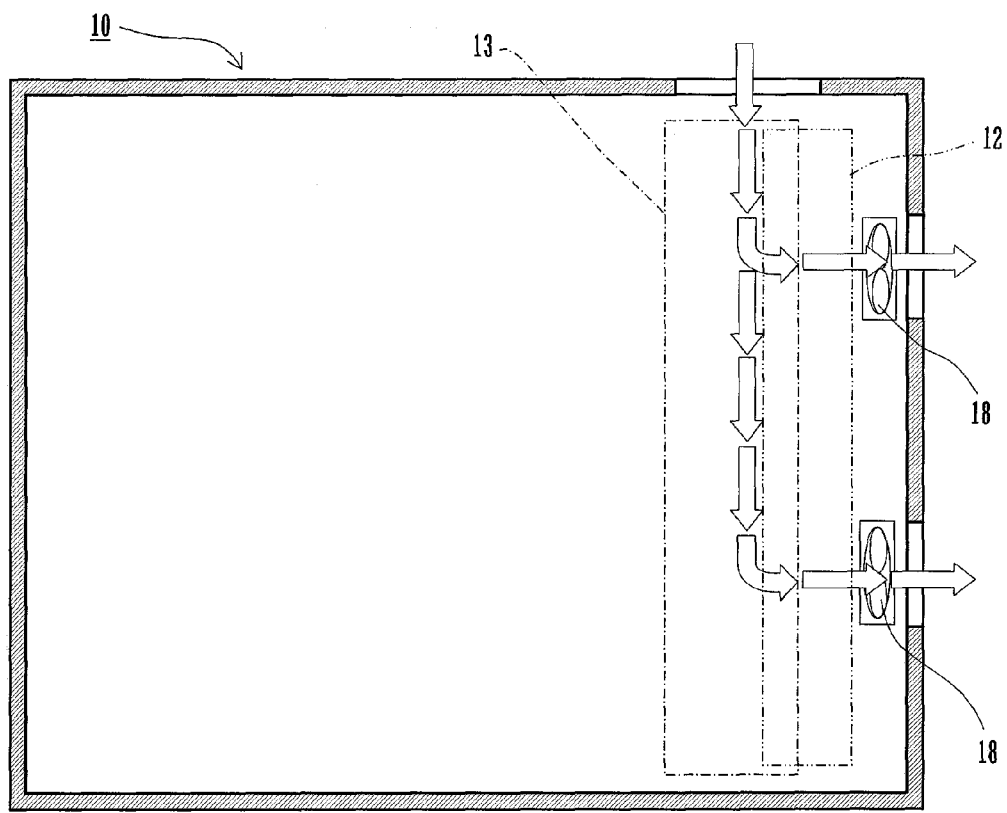
FIG. 6B is a horizontal sectional view of the copier for illustrating the air flow inside the copier.

Referring to FIGS. 6A and 6B, description is made of the relationship between the air intake/exhaust of the housing member 3 and that of the image forming section 10. The ion generating device 70 is disposed inside the housing member 3 which is not in communication with the image forming section 10 and hence is located in the space completely isolated from air that is present inside the image forming section 10. Particularly because the ion generating device 70 is placed so as to be kept from an air flow generated around the electrophotographic processing section 13 and fixing device 12 by the suction of the exhaust fan 18, the ion generating efficiency of the ion generating device 70 is not lowered by contamination of the corona electrodes or the like. Therefore, the ion generating efficiency of the ion generating device 70 can be kept sufficiently high over a long time period.

The air intake portion 302 of the housing member 3 is located on a side (the rear side in the example shown) different from the side of the housing of the image forming apparatus 10 on which the exhaust fan 18 is located. For this reason, air exhausted from the exhaust fan 18 can be prevented from being taken into the housing member 3.

Further, since the filter 66 for cleaning air is located on the air intake side of the duct 64, the corona electrodes of the ion generating device 70 can be more effectively prevented from being contaminated. Therefore, the ion generating efficiency of the ion generating device 70 can be kept high over the entire durable life span of the copier 1.

Figure 7:
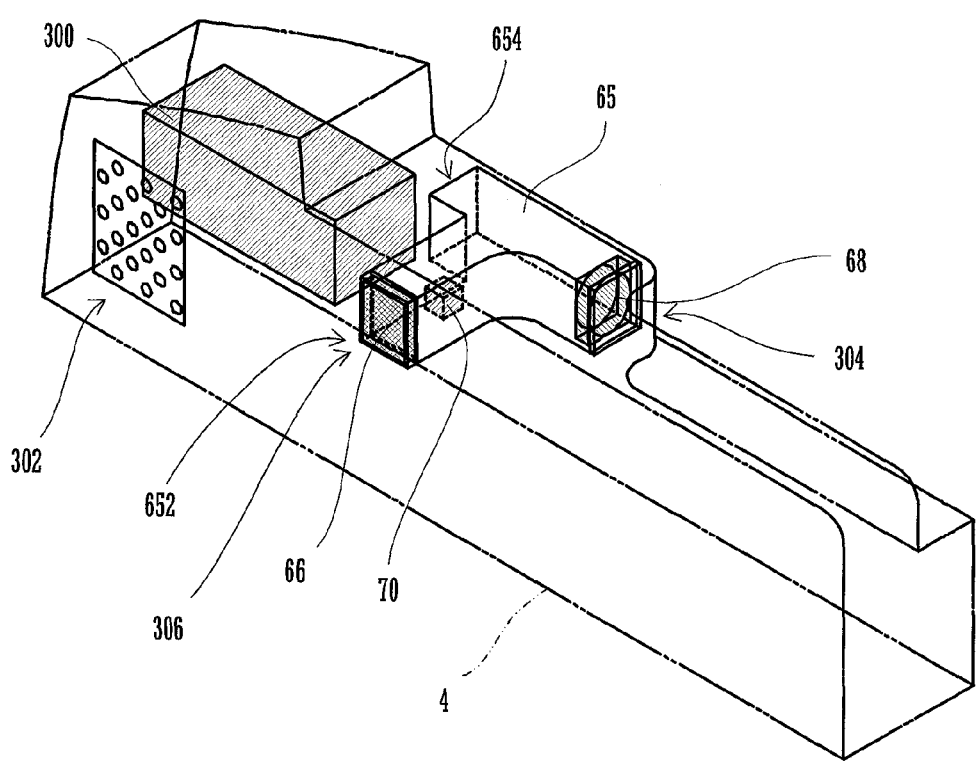
FIG. 7 is a schematic perspective view, as viewed from the rear side, of a variation of the housing member accommodating the driving section therein.

Referring to FIG. 7, description is made of a housing member 4 as a variation of the housing member 3. As shown in FIG. 7, the housing member 4 is different from the housing member 3 in that the housing member 4 has an air intake portion 306 for taking in air to be introduced into the ion generating device 70.

The housing member 4 is internally provided with a duct 65 having a first duct portion 652 and a second duct portion 654. The first duct portion 652 is designed to define a flow path of air that is taken in from the air intake portion 306 and passes toward a fan 68. The second duct portion 654 is designed to define a flow path of air that passes from the air intake portion 302 toward the fan 68 through the driving section 300. The ion generating device 70 is located inside the first duct portion 652. Further, the filter 66 is located at the entrance of the first duct portion 652.

With this arrangement, dust and oil from the driving section 300 can be more effectively prevented from reaching the ion generating device 70 because air that fails to pass through the driving section 300 is introduced into the ion generating device 70. Further, the ion generating device 70 fails to obstruct the flow path of air that passes from the driving section 300 toward the fan 68 and, hence, the driving section 300 can be cooled more effectively.

While the ducts 64 and 65 used in the foregoing embodiments are shaped rectangular in section, use may be made of ducts shaped circular in section or shaped otherwise.

The foregoing embodiments are illustrative in all points and should not be construed to limit the present invention. The is scope of the present invention, is defined not by the foregoing embodiment but by the following claims. Further, the scope of the present invention is intended to include all modifications within the scopes of the claims and within the meanings and scopes of equivalents.

What is claimed is:

1. An image forming apparatus, comprising:
   an automatic document feeder having an ion generating function, comprising:
      a document tray for placing thereon a document to be subjected to reading;
      a document delivery tray for receiving the document having been subjected to reading;
      a document feed path designed to guide the document from the document tray up to the document delivery tray via a document reading position;
      a feeding section configured to apply feeding force onto the document on the document feed path;
      a driving section configured to transmit driving power to the feeding section;
      an automatic document feeder housing member disposed rearwardly of the document tray and the document delivery tray, the automatic document feeder housing member having at least an air intake portion and a first air exhaust portion and being designed to accommodate the driving section therein; and
      an ion generating unit disposed laterally of the driving section within the automatic document feeder housing member and having an ion generating function;
   an image forming section located on a lower side of the automatic document feeder and configured to carry out an electrophotographic image forming process according to image data supplied thereto; and
   an image forming section housing including a second air exhaust portion and being configured to accommodate the image forming section therein,
   wherein:
      the air intake portion of the automatic document feeder housing member is located on a rear side of the image forming apparatus, while the second air exhaust portion of the image forming section housing is located on a side other than the rear side of the image forming apparatus;
      a space in the automatic document feeder housing member is isolated from a space in the image forming section housing;
      the air intake portion includes a first suction portion and a second suction portion;
      the first suction portion is located on an area facing the driving section; and
      the second suction portion is located on an area other than the area facing the driving section.

2. The image forming apparatus according to claim 1, wherein the automatic document feeder further comprises a fan configured to generate a flow of air passing from the air intake portion toward the first air exhaust portion within the automatic document feeder housing member, wherein the driving section and the ion generating unit are located on a flow path of the air passing from the air intake portion toward the first air exhaust portion in the automatic document feeder housing member.

3. The image forming apparatus according to claim 1, wherein the ion generating unit includes:
   an ion generating device configured to generate ions by corona discharge; and
   a filter disposed to intervene between the driving section and the ion generating device.

4. An image forming apparatus, comprising:
   an automatic document feeder, comprising:
      a document tray for placing thereon a document to be subjected to reading;
      a document delivery tray for receiving the document having been subjected to reading;
      a document feed path designed to guide the document from the document tray up to the document delivery tray via a document reading position;
      a feeding section configured to apply feeding force onto the document on the document feed path;
      a driving motor configured to transmit driving power to the feeding section;
      an automatic document feeder housing member disposed rearwardly of the document tray and the document delivery tray, the automatic document feeder housing member having at least a first air intake portion and a first air exhaust portion and being designed to accommodate the driving section motor therein; and
      a fan configured to generate an air flow from the first air intake portion to the first air exhaust portion in the automatic document feeder housing member;
   an image forming section located on a lower side of the automatic document feeder and configured to carry out an image forming process according to image data supplied thereto; and
   an image forming section housing including a fixing device for fixing developer image onto a recording sheet, a second air intake portion and a plurality of second air exhaust portions and being configured to accommodate the image forming section therein,
   wherein:
      the first air intake portion is located on a rear side of the image forming apparatus while the second air intake portion is located on the rear side of the image forming apparatus, and each second air exhaust portion is located on a lateral side of the image forming apparatus, the lateral side being a side of the image forming apparatus near at least the fixing device, thereby the air drawn into the second air intake portion being exhausted from each second air exhaust portion;

a space in the automatic document feeder housing member is isolated from a space in the image forming section housing;
the first air intake portion includes a first suction portion and a second suction portion;
the first suction portion is located on an area facing the driving motor; and
the second suction portion is located on an area other than the area facing the driving motor.

5. The image forming apparatus according to claim 4, wherein the driving motor is located on a flow path of the air passing from the first air intake portion toward the first air exhaust portion in the automatic document feeder housing member.

6. The image forming apparatus according to claim 4, wherein the first air exhaust portion includes an opening for exhausting air and the fan located on an area facing the opening in an upstream side of the opening.

7. The image forming apparatus according to claim 4, wherein the first air intake portion comprises an opening for introducing air, and the opening includes a plurality of holes.

8. An image forming apparatus, comprising:
an automatic document feeder, comprising:
a document tray for placing thereon a document to be subjected to reading;
a document delivery tray for receiving the document having been subjected to reading;
a document feed path designed to guide the document from the document tray up to the document delivery tray via a document reading position;
a feeding section configured to apply feeding force onto the document on the document feed path;
a driving motor configured to transmit driving power to the feeding section;
an automatic document feeder housing member disposed rearwardly of the document tray and the document delivery tray, the automatic document feeder housing member having at least a first air intake portion and a first air exhaust portion and being designed to accommodate the driving motor therein; and
a fan configured to generate an air flow from the first air intake portion to the first air exhaust portion in the automatic document feeder housing member;
an image forming section located on a lower side of the automatic document feeder and configured to carry out an image forming process according to image data supplied thereto; and
an image forming section housing including a second air intake portion and a second air exhaust portion and being configured to accommodate the image forming section therein,
wherein:
the first air intake portion is located on a rear side of the image forming apparatus while the second air intake portion is located on the rear side of the image forming apparatus, and the second air exhaust portion is located on a lateral side of the image forming apparatus, thereby the air drawn into the second air intake portion being exhausted from each second air exhaust portion;
a space in the automatic document feeder housing member is isolated from a space in the image forming section housing;
the first air intake portion is located on an area near an edge side of the automatic document feeder housing member in a longitudinal direction thereof, and the driving motor is configured to face the first air intake portion;
the first air intake portion includes a first suction portion and a second suction portion;
the first suction portion is located on an area facing the driving motor; and
the second suction portion is located on an area other than the area facing the driving motor.

9. The image forming apparatus according to claim 4, wherein the first air exhaust portion is located on an area near a center position of the automatic document feeder housing member in a longitudinal direction thereof.

10. The image forming apparatus according to claim 4, wherein at least one of the plurality of second air exhaust portions includes an opening for exhausting air and a fan located on an area facing the opening in an upstream side of the opening.

11. The image forming apparatus according to claim 4, wherein:
an air exhausting direction from at least one of the plurality of second air exhaust portions is perpendicular to an air exhausting direction from the first air exhaust portion.

12. The image forming apparatus according to claim 4, wherein the first air intake portion and at least a part of the second air intake portion are both located on either right side or left side of the image forming apparatus with respect to a center in a width direction thereof.

13. The image forming apparatus according to claim 8, wherein the driving motor is located on a flow path of the air passing from the first air intake portion toward the first air exhaust portion in the automatic document feeder housing member.

14. The image forming apparatus according to claim 8, wherein the first air exhaust portion includes an opening for exhausting air and the fan located on an area facing the opening in an upstream side of the opening.

15. The image forming apparatus according to claim 8, wherein the first air intake portion comprises an opening for introducing air, and the opening includes a plurality of holes.

16. The image forming apparatus according to claim 8, wherein the first air exhaust portion is located on an area near a center position of the automatic document feeder housing member in a longitudinal direction thereof.

17. The image forming apparatus according to claim 8, wherein the second air exhaust portion includes an opening for exhausting air and a fan located on an area facing the opening in an upstream side of the opening.

18. The image forming apparatus according to claim 8, wherein:
an air exhausting direction from the second air exhaust portion is perpendicular to an air exhausting direction from the first air exhaust portion.

19. The image forming apparatus according to claim 8, wherein the first air intake portion and at least a part of the second air intake portion are both located on either right side or left side of the image forming apparatus with respect to a center in a width direction thereof.

* * * * *